(12) United States Patent
Raby

(10) Patent No.: US 7,033,327 B2
(45) Date of Patent: Apr. 25, 2006

(54) METHOD OF DETERMINING THE LONG AXIS OF AN OBJECT

(75) Inventor: Richard E. Raby, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 318 days.

(21) Appl. No.: 10/243,362

(22) Filed: Sep. 13, 2002

(65) Prior Publication Data

US 2004/0054304 A1    Mar. 18, 2004

(51) Int. Cl.
*A61B 5/103* (2006.01)
*A61B 5/117* (2006.01)

(52) U.S. Cl. .......................... 600/590; 433/2
(58) Field of Classification Search ................ 600/587, 600/590; 433/24, 229, 213, 223; 703/1, 703/11; 702/155
See application file for complete search history.

(56) References Cited

U.S. PATENT DOCUMENTS

| | | | |
|---|---|---|---|
| 4,766,556 A | 8/1988 | Arakawa | |
| 5,220,398 A | 6/1993 | Horn et al. | |
| 5,395,238 A | 3/1995 | Andreiko et al. | |
| 5,431,562 A | 7/1995 | Andreiko et al. | |
| 5,454,717 A | 10/1995 | Andreiko et al. | |
| RE35,169 E | 3/1996 | Lemchen et al. | |
| 5,533,895 A | 7/1996 | Andreiko et al. | |
| 5,850,468 A | 12/1998 | Yokoyama et al. | |
| 6,099,313 A | 8/2000 | Dörken et al. | |
| 6,123,544 A | 9/2000 | Cleary | |
| 6,261,098 B1 | 7/2001 | Persson | |
| 6,358,052 B1 | 3/2002 | Lustig et al. | |
| 2002/0006597 A1 | 1/2002 | Andreiko et al. | |

FOREIGN PATENT DOCUMENTS

| | | |
|---|---|---|
| EP | 0364243 | 4/1990 |
| WO | WO 00/19935 | 4/2000 |

OTHER PUBLICATIONS

A Method for Working out the Moments of a Polygon Using an Integration Technique, 1990, Elsevier Science Publishers, pp. 351-354.

Measurement of the Inertia Tensor: An Experimental Proposal, Elsevier Science B.V., 1995, pp. 241-254.

(Continued)

*Primary Examiner*—Max F. Hindenburg
*Assistant Examiner*—Brian Szmal
(74) *Attorney, Agent, or Firm*—James D. Christoff

(57) ABSTRACT

The long axis of an object that is complex in shape, such as a tooth, may be accurately determined using digital data representing the shape of the object. A polyhedron is defined such that the center of the polyhedron coincides with a point representing the centroid of the object. Axis lines are then determined by establishing reference lines through each face of the polyhedron and the point representing the centroid of the object. The moment of the object is calculated about each axis line, and the axis line that corresponds to the smallest calculated moment is selected. Additional iterations of the method are then carried out by recursively subdividing the corresponding face into smaller sections until a desired angular accuracy is achieved. The method is particularly useful for orthodontic diagnosis and treatment.

58 Claims, 5 Drawing Sheets

OTHER PUBLICATIONS

Calculating Geometric Properties of Objects, Represented by Fourier Coefficients, N. Kiryati, Department of Electrical Engineering, Technion-Israel Institute of Technology, 1988, pp. 641-646.

Pending PCT Patent Application No. US02/14022, filed May 1, 2002.

Pending U.S. Appl. No. 09/965,707, filed Sep. 26, 2001.

Pending U.S. Appl. No. 10/081,220, filed Feb. 22, 2002.

Direct Least-Squares Fitting of Algebraic Surfaces, Vaughan Pratt, Computer Graphics, vol. 21, No. 4, Jul. 1987.

Surface Reconstruction from Unorganized Points, Computer Graphics, 26, Jul. 2, 1992.

Geometric least-squares fitting of spheres, cylinders, cones and tori, G. Lukacs et al., May 23, 1997.

Introductory Literature Review, Surface Reconstruction from Three Dimensional Range Data, Andrew Myers, Apr. 1999, pp. 1-15.

Perform Multivariate Linear Regression with Mathematica, Wolfram Research, pp. 1-5, printed Jul. 18, 2002.

Munich Heart-Our Cardiac Analysis Package, Version 26, Dec. 1998, pp. 1-3.

Fitting of myocardial wall for estimating the fractional volume of infarcted tissue in dual-tracer PET, 3 pages, printed Jul. 18, 2002.

Welcome to the Division of Physiological Imaging 3D Galleryl, 4 pages, printed Jul. 18, 2002.

Volumetric Image Display and Analysis (VIDA) Table of Contents, VIDA®-:an overview, printed Jul. 18, 2002.

IEEE, Pattern Analysis and Machine Intelligence, 3D Moment Forms: Their Construction and Application to Object Identification and Positioning, 1 page, 1989.

Pattern Recognition of 3D CAD Objects: Toward an Electronic Yellow Pages of Mechanical Parts*, Cybenko et al., 1997, Smart Engineering Systems Design, vol. 1, pp. 1-13, Jan. 25. 1996.

Practical Algorithms for Image Analysis, Description, Examples and Code, Seul et al., Cambridge University Press, 2000, pp. 146-151.

The HarperCollins Dictionary of Mathematics, Moment Generating Function, Monotone, Modular Function, Moment; Borowski et al., 1991, pp. 386-385.

Chapter 18.2: Multiple Integrals; Calculus and Analytic Geometry_, 7th ed., by George B. Thomas, Jr. and Ross L. Finney, Addison-Wesley Publishing Company, Reading, Massachusetts, copyright 1988, pp. 970-974.

"Gravitational collapse and moment of inertia of regular polyhedral configurations"; P.K. Aravind; American Journal of Physics, vol. 59, N. 7, 1991, pp. 647-652.

Landmark identification error in submentovertex cephalometrics, A computerized method for determining the condylar long axis; Philip C. Williamson et al.; Oral Surgery Oral Medicine Oral Pathology Oral Radiology, vol. 88, No. 3, Sep. 1998.

METHOD OF DETERMINING THE LONG AXIS OF AN OBJECT

BACKGROUND OF THE INVENTION

1. Field of the Invention

This invention relates to a method of determining the longitudinal reference axis of an object. The method is particularly suitable for use with a computer software module that finds the long axis of a tooth as part of an orthodontic diagnosis and treatment analysis.

2. Description of the Related Art

The longitudinal axis, or long axis, of objects that are relatively simple in shape is often easy to determine. For example, the long axis of an object having a uniform circular or rectangular shape in transverse cross-sections can be derived by extending a reference line perpendicularly through the center of the cross-sections. However, the long axis of an object that is complex in shape may be substantially more difficult to determine.

For example, teeth are generally considered to be complex in shape. The exposed portion of each tooth, also known as the clinical crown, varies widely from tooth to tooth. For instance, incisal teeth generally taper to an outer edge resembling a chisel blade while cuspid teeth generally taper to a point, called a cusp. Bicuspid teeth have two outer cusps that are separated by a recess, while molar teeth typically have four cusps.

Additionally, the roots of the teeth vary from one tooth to another. Anterior and cuspid teeth typically have one root while bicuspid teeth often have two roots. The molar teeth usually have three roots.

Moreover, it is known that the shape of teeth can vary widely from one patient to the next. While teeth generally have certain common characteristics (for example, the cuspid teeth typically have a single root and taper to an outer occlusal point), the exact shape of a cuspid tooth can vary considerably from one patient to another when closely inspected.

In the field of dentistry, there is often a desire to establish the long axis of one or more teeth in order to facilitate diagnosis and/or treatment. For example, the field of orthodontics is concerned with repositioning and aligning the patient's teeth for improved occlusion and aesthetic appearance. The long reference axis (longitudinal axis) of a tooth can serve as a convenient shorthand description for identifying the tooth's actual or desired orientation.

Establishing the long axis of the tooth provides other benefits for the orthodontic practitioner as well. For example, orthodontic treatment often involves the use of tiny slotted appliances, known as brackets, that are fixed to the patient's anterior, cuspid, and bicuspid teeth. An archwire is received in the slot of each bracket and serves as a track to guide movement of the teeth to desired orientations. The ends of the archwires are usually received in appliances known as buccal tubes that are secured to the patient's molar teeth.

A number of orthodontic appliances in commercial use today are constructed on the principle of the "Straight Wire Concept" developed by Dr. Lawrence F. Andrews, D.D.S. In accordance with this concept, the shape of the appliance, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

As can be appreciated, it is important for the practitioner using straight wire appliances to fix each appliance in the exact proper position on the corresponding tooth. If, for example, the bracket is placed too high in an occlusal direction on the tooth surface, the archwire will tend to position the crown of the tooth too close to the gingiva (gums) at the end of treatment. As another example, if the bracket is placed to one side of the center of the tooth in a mesial-distal direction, the resultant tooth orientation will likely be an orientation that is excessively rotated about its long axis.

As a consequence, practitioners in the past have often taken considerable care when bonding straight wire appliances to the patient's teeth to ensure that the appliances are precisely positioned on the teeth at correct locations. Some practitioners prefer to place each appliance on the location that is known as the facial axis point of the tooth. Unfortunately, visual determination of the facial axis point is often difficult to carry out with precision and may be subjective in nature.

In theory, the facial axis point of the tooth crown is defined as the intersection of the mid-transverse plane, the mid-sagittal plane, and the facial surface of the clinical crown. The mid-sagittal plane is a reference plane that includes the long axis of the tooth and separates the mesial and distal halves of the clinical crown. The mid-transverse plane of the crown is perpendicular to the long axis of the tooth and separates the occlusal and gingival halves of the clinical crown. In practice, however, such a determination is difficult to carry out with a high level of accuracy when a visual assessment is employed.

In recent years, there has been increased interest in the use of digital microcomputers and software for orthodontic diagnosis and treatment. For example, placement of orthodontic brackets using either direct bonded or indirect bonded techniques can be carried out with much greater precision using microcomputers and robotics than can be accomplished by visual placement techniques. Clearly, such increased placement accuracy of orthodontic appliances significantly increases the likelihood that the teeth will be properly positioned at the conclusion of orthodontic treatment.

Digital microcomputers and software are also highly useful in treatment diagnosis and planning. For example, data representing the shape and orientation of the patient's teeth may be processed by a microcomputer to help predict the appearance of the teeth at the conclusion of treatment or at various stages during the course of treatment. This data may also be used to predict the path of movement of the teeth as treatment progresses.

Presently, there is a need in the art to have an automated method for determining the long axis of an object that is complex in shape, such as a tooth. Preferably, the method would eliminate subjective factors that have typically been associated with certain visual long axis determinations in the past. Further, any such method should be usable in the field of dentistry with any desired tooth without regard for the number of roots or the shape of the clinical crown.

SUMMARY OF THE INVENTION

The present invention relates to a method of determining the long axis of an object and is especially useful as computer software. The method provides a geometric analysis that is capable of determining the long axis of a variety of objects that are complex in shape, such as teeth. In particular, the method can be used to determine the long axis of a variety of teeth of different types and shapes without the need for subjective input from the practitioner. The method is particularly useful for orthodontic diagnosis and treatment, since the long axes of a patient's teeth can be used in a program that aids in the precise placement of orthodontic appliances on the surfaces of the teeth or that predicts the paths of movement and future positions of the teeth.

According to one embodiment of the present invention, a method of determining the long axis of an object comprises:

defining a polyhedron that surrounds a point representing the centroid of the object;

defining, for at least some of the faces of the polyhedron, an axis line that passes through the face and also through the point representing the centroid of the object;

calculating the moment of the object about each axis line; and selecting the axis line that corresponds to the smallest calculated moment.

In another embodiment of the invention, a method of determining the long axis of an object comprises:

(a) providing a set of data representing the shape of an object;

(b) defining a polyhedron that surrounds a point representing the centroid of an object;

(c) defining, for at least sonic of the faces of the polyhedron, an axis line that passes through the face and also through the point representing the centroid of the object;

(d) calculating the moment of the object about each axis line;

(e) selecting the axis line that corresponds to the smallest calculated moment;

(f) determining the angle between the selected axis line and a reference line defined by a vertex of the polyhedron face associated with the selected axis line;

(g) comparing the determined angle to a pre-selected value; and (h) recursively following, by subdividing into sections the face corresponding to the selected axis line, at least some of acts a–g if the determined angle is greater than the preselected value.

Another embodiment of the present invention is directed toward a method of determining the long axis of a tooth. This method comprises:

(a) providing a set of data representing the shape of a tooth;

(b) defining a polyhedron that surrounds a point representing a centroid of a tooth;

(c) defining, for at least some of the faces of the polyhedron, an axis line that passes through the face and also through the point representing the tooth centroid;

(d) calculating the moment of the tooth about each axis line;

(e) selecting the axis line that corresponds to the smallest calculated moment;

(f) determining the angle between the selected axis line and a reference line defined by a vertex of the polyhedron face associated with the selected axis line;

(g) comparing the determined angle to a pre-selected value; and (h) recursively following, by subdividing into sections the face corresponding to the selected axis line, at least some of acts a–g if the determined angle is greater than the pre-selected value.

The long axis can be determined to any desired degree of precision by additional iterations of the acts set out above. For example, in the method set out in the immediately preceding paragraph, the subdivided section of the face of the polyhedron associated with the axis line corresponding to the smallest calculated moment can be further divided into additional subdivided sections, and new axis lines can then be defined for each newly subdivided section. By following such practice, the resultant determined angle becomes smaller with each iteration until such time as the angle is sufficiently small and the resultant accuracy is deemed satisfactory.

Further aspects of the invention are set out in the detailed description that follows and are illustrated in the accompanying drawings.

DETAILED DESCRIPTION OF THE PREFERRED EMBODIMENTS

Figure 1:
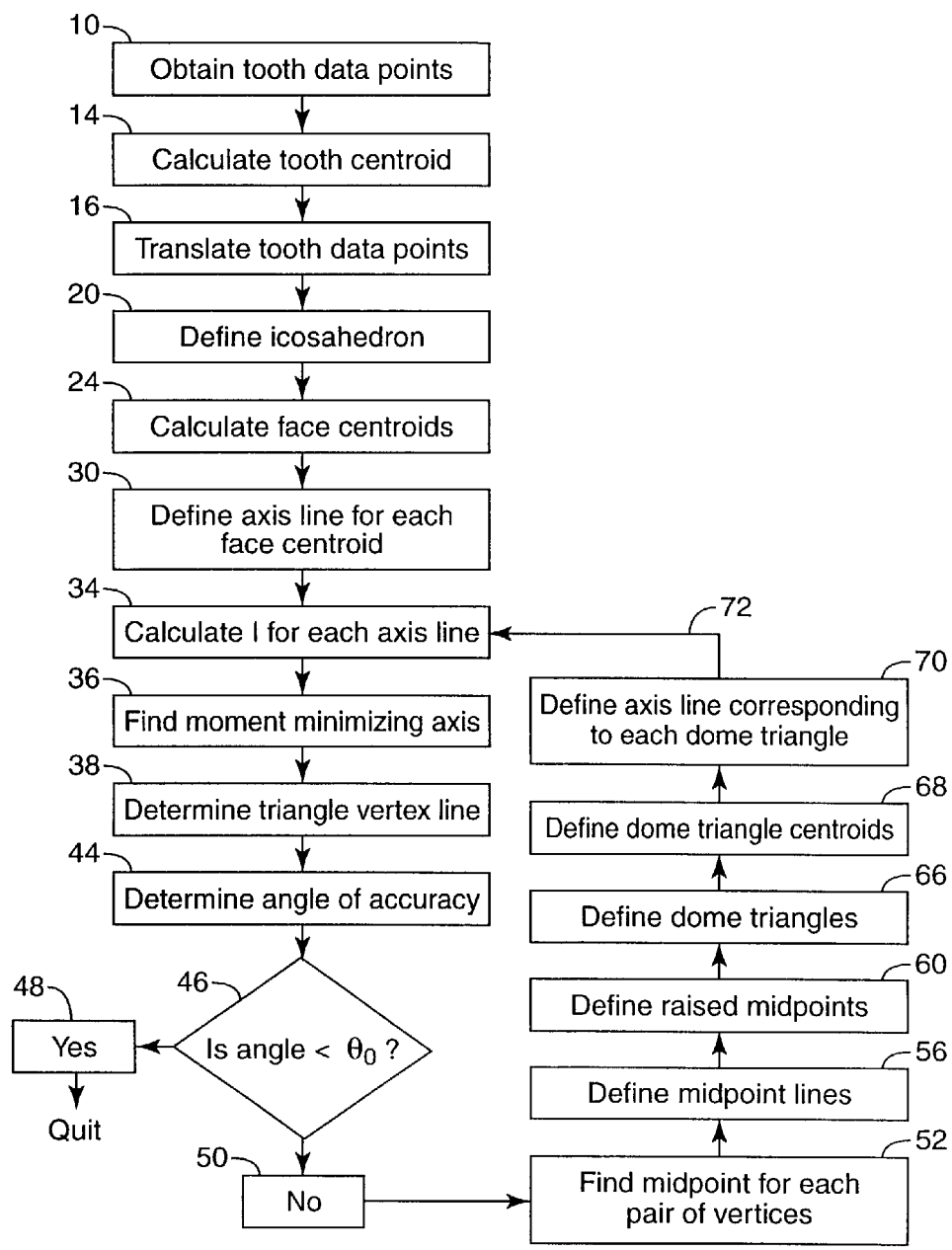
FIG. 1 is a flow chart summarizing a method for determining the long axis of a tooth according to one embodiment of the present invention.

A method of determining the long axis of an object according to one embodiment of the present invention is set out in the flow chart illustrated in FIG. 1. In the particular embodiment described in FIG. 1, the object is a tooth of a dental patient. However, the present invention may be used to find the long axis of other objects as well.

In FIG. 1, Box 10 describes the act of obtaining a set of data points that represent a tooth. The data points may represent points on the outer surface of the tooth including the crown (i.e., the part normally exposed and not covered by gingiva) as well as the root or roots (i.e., the part normally not exposed). As another option, the data set may represent points that are uniformly or non-uniformly distributed throughout the volume occupied by the tooth. As an additional alternative, the set of data points may represent any combination of the foregoing.

The data points may be obtained by any suitable method. For example, the data points may be provided by use of a computed tomography scanner (CT scanner). As another alternative, a set of data points representing the patient's tooth crown may be obtained by use of an intra-oral scanner that scans the patient's actual tooth or by use of an extra-oral scanner that scans a model of the patient's tooth or an impression of the tooth. Optionally, the set of data points representing the tooth crown can be married to a set of data points representing model teeth roots such as is described in PCT published application No. PCT/IUS02/14022, which is incorporated by reference herein. As another alternative, the data points and the resultant determined long axis may represent only a portion of the tooth, such as the clinical crown.

Figure 2:
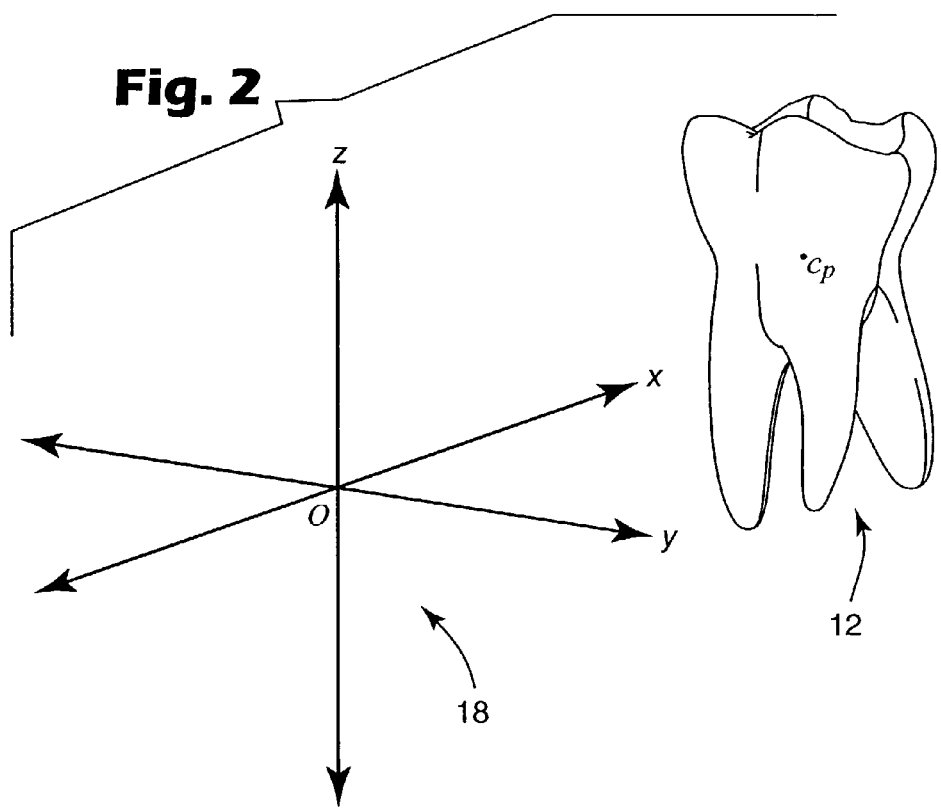
FIG. 2 is an exemplary illustration showing an outline of a tooth defined by a number of data points along with a three-axis coordinate system useful in carrying out the method described in FIG. 1.

FIG. 2 is an exemplary illustration of a set of data points representing the exterior surface of a tooth 12. In this instance, the tooth 12 is a first molar tooth, although other teeth may be used as well. The exterior surface includes the portion of the tooth that is normally visible (i.e., the clinical crown), as well as the sub-gingival portion of the tooth that is normally not visible (i.e., the root or roots).

In mathematical terms, the tooth data set P is comprised of a set of n points in three-dimensional space, where each point $p_i$ is defined as $$p_i = (x_i, y_i, z_i), \text{ where } 0 \leq i < n.$$

Next, and as represented by Box 14 in FIG. 1, the centroid of the tooth 12 is determined. As an example, the centroid $c_P$ may be determined by calculating the arithmetic mean of the tooth data points P in three-dimensional space. For instance, $$c_P = (x_c, y_c, z_c), \text{ where } x_c = \sum_{i=0}^{n-1} x_i, \ y_c = \sum_{i=0}^{n-1} y_i, \text{ and } z_c = \sum_{i=0}^{n-1} z_i.$$

Figure 3:
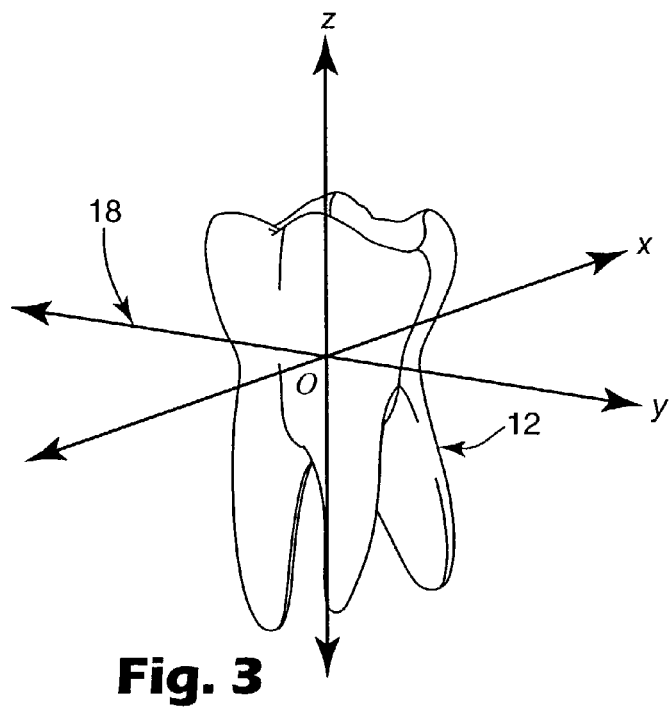
FIG. 3 is a view similar to FIG. 2 except that the data points representing the tooth have been translated so that the centroid of the tooth is at the origin of the coordinate system.

As illustrated by Box 16 in FIG. 1, the tooth data points are then translated relative to a three-axis coordinate system so that the tooth centroid $c_P$ is located at the origin O of the coordinate system. As an example, the set of data points representing tooth 12 in FIG. 2 is translated relative to the coordinate system 18 so that the tooth centroid coincides with the origin of the coordinate system 18 as shown in FIG. 3. As an alternative, it may be possible to translate the coordinate system 18, or to translate both the data points and the coordinate system so that the centroid of the tooth and the origin of the coordinate system coincide.

Figure 4:
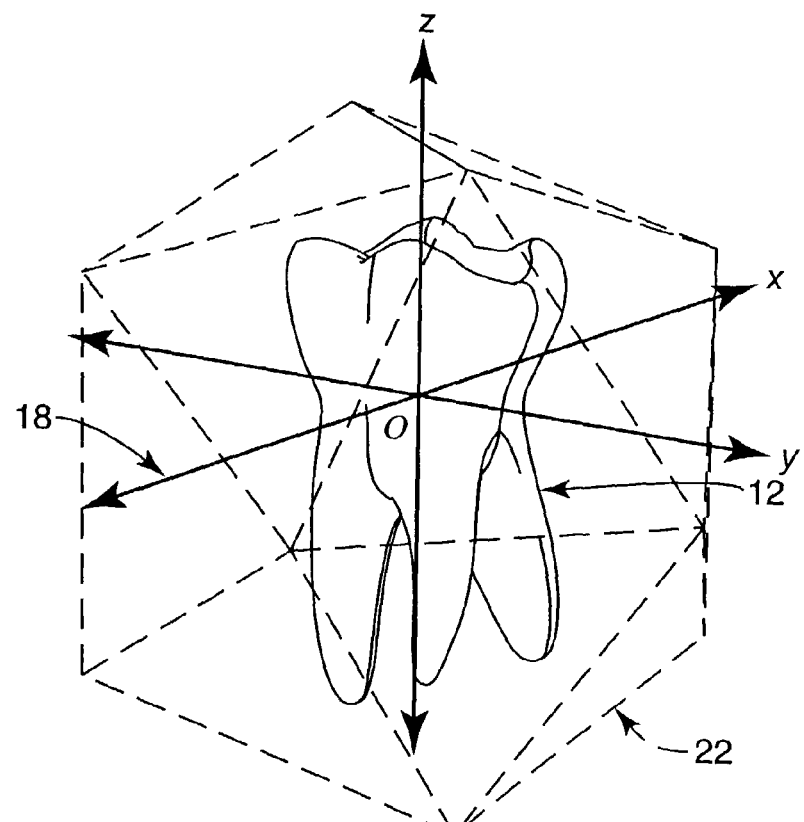
FIG. 4 is an illustration similar to FIG. 3, additionally showing an icosahedron in dashed lines that has been established such that the center of the icosahedron is at the origin of the coordinate system.

Subsequently, and as indicated by Box 20 in FIG. 1, an icosahedron is defined such that the center of the icosahedron coincides with the origin of the coordinate system 18. An exemplary icosahedron 22 is illustrated in FIG. 4 in surrounding relationship to the set of data points representing the tooth 12. The orientation of the icosahedron 22 relative to the coordinate system 18 is not important, so long as the center of the icosahedron coincides with the origin of the coordinate system 18. Additionally, the icosahedron 22 may be smaller than the space enclosed by the set of data points representing the tooth 12, and the icosahedron 22 need not surround the data points.

The icosahedron 22 has twelve vertices $v_{ico_0}$, $v_{ico_1}$, ..., $v_{ico_{11}}$ that are defined as follows:

$$\phi = \frac{1 + \sqrt{5}}{2}$$

(also known as the "golden ratio")

$v_{ico_0} = (0, -1/\phi, 1)$
$v_{ico_1} = (1/\phi, -1, 0)$
$v_{ico_2} = (1, 0, 1/\phi)$
$v_{ico_3} = (0, 1/\phi, 1)$
$v_{ico_4} = (-1, 0, 1/\phi)$
$v_{ico_5} = (-1/\phi, -1, 0)$
$v_{ico_6} = (0, -1/\phi, -1)$
$v_{ico_7} = (1, 0, -1/\phi)$
$v_{ico_8} = (1/\phi, 1, 0)$
$v_{ico_9} = (-1/\phi, 1, 0)$
$v_{ico_{10}} = (-1, 0, -1/\phi)$
$v_{ico_{11}} = (0, 1/\phi, -1)$ The icosahedron 22 has twenty triangular faces $F_0$, $F_1$, ..., $F_{19}$, where each face is defined in terms of three specific vertices from the previously defined set of vertices $v_{ico_0}$, $v_{ico_1}$, ..., $v_{ico_{11}}$. The faces of the icosahedron are defined as follows:

$F_0 = \{v_{ico_0}, v_{ico_1}, v_{ico_2}\}$
$F_1 = \{v_{ico_0}, v_{ico_2}, v_{ico_3}\}$
$F_2 = \{v_{ico_0}, v_{ico_3}, v_{ico_4}\}$
$F_3 = \{v_{ico_0}, v_{ico_4}, v_{ico_5}\}$
$F_4 = \{v_{ico_0}, v_{ico_5}, v_{ico_1}\}$
$F_5 = \{v_{ico_1}, v_{ico_6}, v_{ico_7}\}$
$F_6 = \{v_{ico_1}, v_{ico_7}, v_{ico_2}\}$
$F_7 = \{v_{ico_2}, v_{ico_7}, v_{ico_8}\}$
$F_8 = \{v_{ico_2}, v_{ico_8}, v_{ico_3}\}$
$F_9 = \{v_{ico_3}, v_{ico_8}, v_{ico_9}\}$
$F_{10} = \{v_{ico_3}, v_{ico_9}, v_{ico_4}\}$
$F_{11} = \{v_{ico_4}, v_{ico_9}, v_{ico_{10}}\}$
$F_{12} = \{v_{ico_4}, v_{ico_{10}}, v_{ico_5}\}$
$F_{13} = \{v_{ico_5}, v_{ico_{10}}, v_{ico_6}\}$
$F_{14} = \{v_{ico_5}, v_{ico_6}, v_{ico_1}\}$
$F_{15} = \{v_{ico_6}, v_{ico_{11}}, v_{ico_7}\}$
$F_{16} = \{v_{ico_7}, v_{ico_{11}}, v_{ico_8}\}$
$F_{17} = \{v_{ico_8}, v_{ico_{11}}, v_{ico_9}\}$
$F_{18} = \{v_{ico_9}, v_{ico_{11}}, v_{ico_{10}}\}$
$F_{19} = \{v_{ico_{10}}, v_{ico_{11}}, v_{ico_6}\}$ Note that a polyhedron other than an icosahedron may be used in the practice of the present invention. For example, a tetrahedron or octahedron may be used as an alternative. A polyhedron with non-triangular faces may also be utilized, such as a cube or dodecahedron. Furthermore, the faces of the polyhedron need not be regular (equal in size and shape) or limited in number. However, polyhedrons with triangular or quadrilateral faces are preferred in order to carry out the recursive subdivision as will be explained in the paragraphs that follow.

Figure 5:
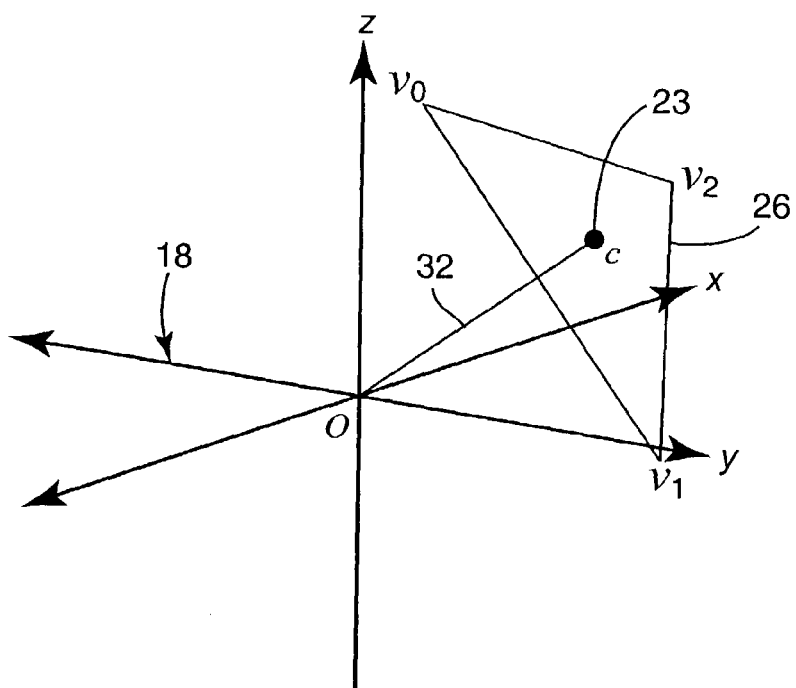
FIG. 5 is a view of the coordinate system and an exemplary face of the icosahedron shown in FIG. 4, additionally depicting an axis line that has been established through the centroid of the face as well as through the origin of the coordinate system.
Figure 6:
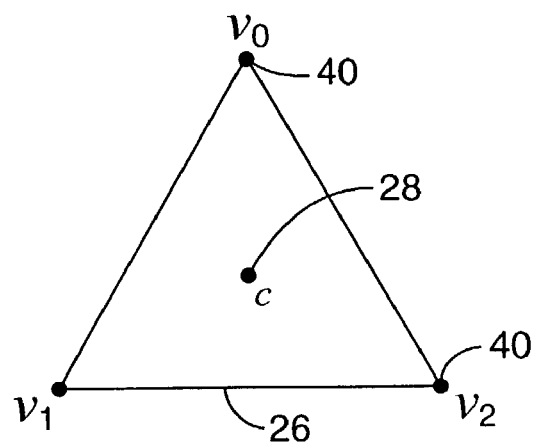
FIG. 6 is a partially rotated elevational view of the face alone that is shown in FIG. 5.

Next, and as represented by Box 24 in FIG. 1, the centroid of each triangular face $F_0, F_1, \ldots, F_{19}$, of the icosahedron 22 is determined, resulting in centroids $c_{F_0}, c_{F_1}, \ldots c_{F_{19}}$. An exemplary face 26 is illustrated in FIG. 5, and an elevational view of the same face 26 is depicted in FIG. 6. The calculated centroid 28 of the face 26 is also shown in FIGS. 5 and 6. In particular, the centroids are defined as follows:

$$c_{F_0} = \text{centroid}(F_0)$$
$$c_{F_1} = \text{centroid}(F_1)$$
$$\vdots$$
$$c_{F_{19}} = \text{centroid}(F_{19}).$$

Subsequently, and as indicated by Box 30 in FIG. 1, an axis line 32 is defined for each face centroid $c_{F_0}, c_{F_1}, \ldots, c_{F_{19}}$. As illustrated in FIG. 5, the axis line 32 extends through the centroid 28 of face 26 as well as through the origin of the coordinate system 18. The axis line 32 for each triangular face 26 is defined as follows:

$$R_{F_0} = \text{ray}(O, c_{F_0})$$
$$R_{F_1} = \text{ray}(O, c_{F_1})$$
$$\vdots$$
$$R_{F_{19}} = \text{ray}(O, c_{F_{19}}).$$

Next, and as represented by Box 34 in FIG. 1, a moment I (such as the first or second moment or moment of inertia) of the tooth 12 defined by points P is calculated about each axis line $R_{F_0}, R_{F_1}, \ldots, R_{F_{19}}$. Thus, each moment is defined as follows:

$$I_{F_0} = \text{moment}(P, R_{F_0})$$
$$I_{F_1} = \text{moment}(P, R_{F_1})$$
$$\vdots$$
$$I_{F_{19}} = \text{moment}(P, R_{F_{19}}).$$

The face centroid, the axis line, and the moment about the axis line are calculated for each triangular face of the icosahedron 22. Since the icosahedron has twenty triangular faces, a total of twenty moments, each corresponding to one of the twenty defined axis lines, will be obtained.

As another option, the face centroid, the axis line, and the moment are determined for fewer than all of the triangular faces. For example, faces of an icosahedron that are opposite one another will have identical axis lines that result in identical moment calculations. Consequently, for regular polyhedrons, only the faces in one hemisphere need be examined. As another example, a practitioner using the method could visually assess the shape of the object on a computer display and enter an estimated orientation of the long axis, and the program could therefore narrow its initial calculations to axis lines that approximate the orientation of the estimated long axis.

Subsequently, and as represented by Box 36 in FIG. 1, the axis line is selected that minimizes the moment of the tooth. This axis line, also called the "moment-minimizing axis", is determined as follows:

$I_j = \min(|I_{F_0}|, |I_{F_1}|, \ldots, |I_{F_{19}}|)$.

Note that absolute values are to be taken from the moments $I_{F_0}, I_{F_1}, \ldots, I_{F_{19}}$ prior to finding the minimum, in case the moments are calculated in such a way as to result in negative values. The subscript j shall assume the value of the subscript assigned to the face associated with the moment-minimizing axis for the remainder of this iteration. Furthermore, the labels $v_0$, $v_1$, and $v_2$ shall be assigned arbitrarily to the vertices of the face associated with the moment-minimizing axis, and these vertices will be referred to as such for the remainder of this iteration. Next, a triangle vertex line is determined as described in Box 38 of FIG. 1. The triangle vertex line is defined by the origin O and any vertex of the face 26 that is associated with the moment-minimizing axis line determined in Box 36. That is:

$R_{F_v} = \text{ray}(O, v_0)$ or
$R_{F_v} = \text{ray}(O, v_1)$ or
$R_{F_v} = \text{ray}(O, v_2)$.

Figure 7:
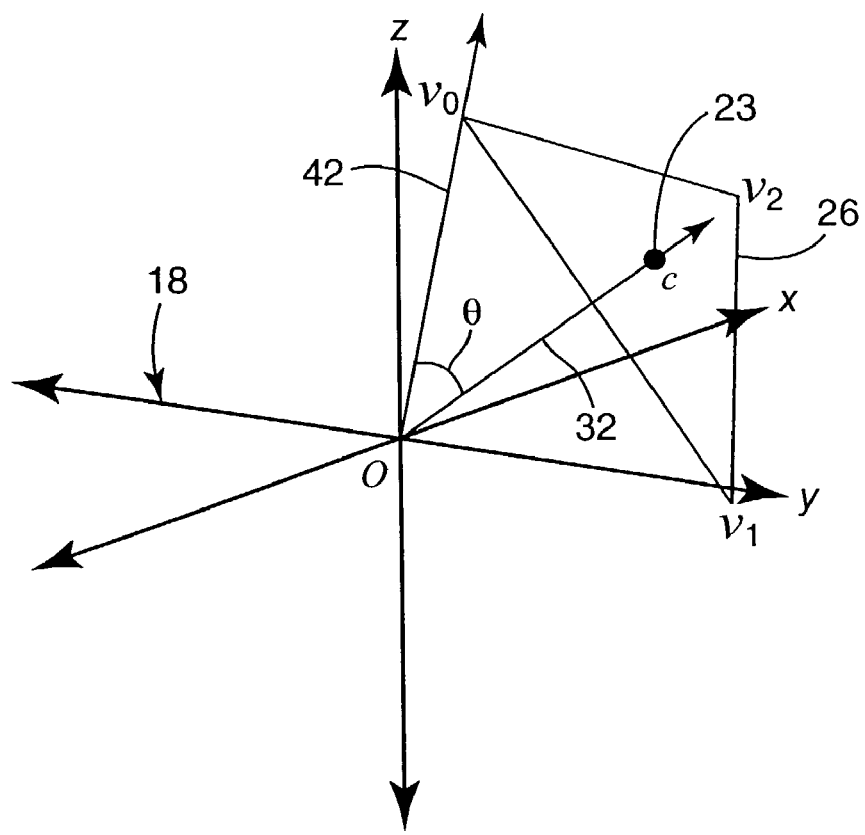
FIG. 7 is a view similar to FIG. 5 but showing an additional reference line that has been established through one of the vertices of the triangular face and the origin of the coordinate system along with an angle identified as the angle between that line and the line passing through the centroid of the face.

In FIGS. 6 and 7, the vertices of the triangular face 26 are identified by the numeral 40, and an exemplary triangle vertex line $R_{F_v}$ is identified by the numeral 42 in FIG. 7.

Subsequently, and as indicated by Box 44 in FIG. 1, the angle of accuracy is calculated. The angle of accuracy is determined by finding the angle between the vertex line 42 and the axis line 32. This angle is designated "θ" in FIG. 7 and is defined as follows:

$\theta = \text{angle}(R_{F_v}, R_j)$.

Next, and as shown by Box 46 in FIG. 1, a computation is performed to determine whether or not the angle θ found in the previous step is less than a predefined angular accuracy $\theta_0$. If the answer is yes, the desired determination is complete as indicated by Box 48 in FIG. 1, and the axis line 32 can then be designated as the long axis of the tooth 12. If the answer is no, as indicated by Box 50 in FIG. 1, the method proceeds to Box 52 for additional steps.

In practice, Box 48 will not be reached after the first comparison of θ to $\theta_0$ in Box 46 unless the long axis is found within a predetermined angular accuracy $\theta_0$ by coincidence. As will be explained in the paragraphs below, it is preferable, in most instances, to increase the degree of precision, and, as a result, Box 48 will be reached only after one or more iterations of the boxes that follow Box 50.

Box 52 represents the step of finding the midpoint of each pair of vertices of the triangular face j 26 that is associated with the previously calculated moment-minimizing axis determined by Box 36. The midpoints are designated by the numerals 54 in FIG. 8, and are defined as follows:

$m_{01} = \text{midpoint}(v_0, v_1)$
$m_{12} = \text{midpoint}(v_1, v_2)$
$m_{20} = \text{midpoint}(v_2, v_0)$.

Figure 8:
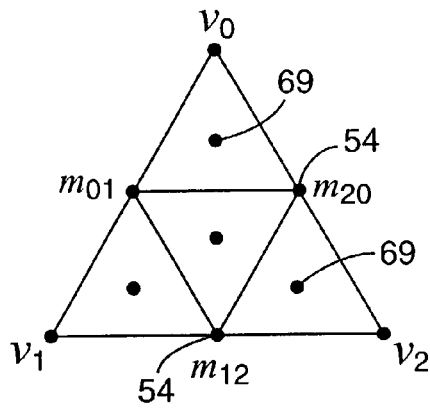
FIG. 8 is a view similar to FIG. 6 except that the face has been subdivided into three smaller triangular sections.
Figure 9:
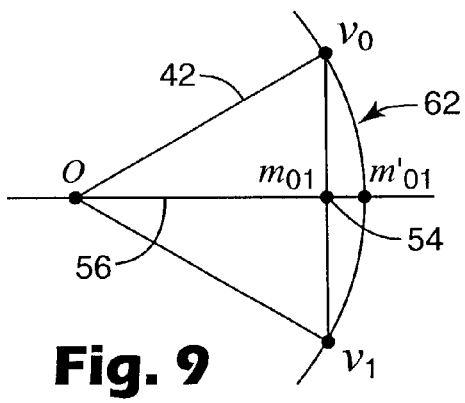
FIG. 9 is a view looking in a perpendicular direction toward the face depicted in FIG. 8.

Subsequently, and as indicated by Box 56 in FIG. 1, midpoint lines are defined for each of the midpoints 54. Each midpoint line passes through one of the midpoints 54 and the origin of the coordinate system 18. An exemplary midpoint line 56 is shown in FIG. 9, which is a view taken in a plane perpendicular to the plane of illustration of FIG. 8. The midpoint lines are defined as follows:

$R_{m01} = \text{ray}(O, m_{01})$
$R_{m12} = \text{ray}(O, m_{12})$
$R_{m20} = \text{ray}(O, m_{20})$.

Next, and as indicated by Box 60 in FIG. 1, the location of a "raised midpoint" for each midpoint line is determined.

Figure 10:
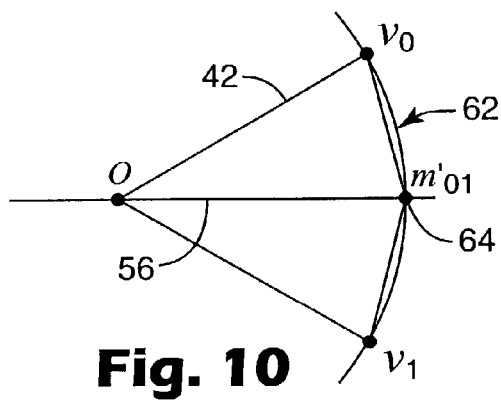
FIG. 10 is a view similar to FIG. 9 except that the midpoints of the original triangular face have been raised to become tangent to a reference sphere to which the vertices of the icosahedron are also tangent.

To find a raised midpoint, a reference sphere is established having a center that coincides with the origin O of the coordinate system 18 and having a radius such that every vertex of the icosahedron is tangent to the sphere. Each raised midpoint $m'_{01}$, $m'_{12}$, and $m'_{20}$ is located at the intersection of its midpoint line $R_{m_{01}}$, $R_{m_{12}}$, and $R_{m_{20}}$, respectively, and the sphere S. The sphere is represented by the numeral 62 in FIGS. 9 and 10, and the raised midpoint for the midpoint line 56 is designated by the numeral 64 in FIG. 10. The raised midpoints are defined as follows:

$m'_{01}$=raysphereintersection($R_{m_{01}}$, S)
$m'_{12}$=raysphereintersection($R_{m_{12}}$, S)
$m'_{20}$=raysphereintersection($R_{m_{20}}$, S).

Next, and as represented by Box 66 in FIG. 1, the face 26 is subdivided into sections. More particularly, the triangular face 26 is subdivided into four smaller triangles as shown in FIG. 8. The vertices of the central triangle $T_3$ consist of the raised midpoints 64 as defined by Box 60. The vertices of the remaining three triangles $T_0$, $T_1$, $T_2$ are defined by one of the vertices 40 of the original face 26 as well as the two raised midpoints 64 adjacent to this vertex 40. Each of the four smaller triangles defined in this step is designated a "dome triangle". The dome triangles are defined as follows:

$T_0 = \{v_0, m_{01}, m_{20}\}$
$T_1 = \{v_1, m_{12}, m_{01}\}$
$T_2 = \{v_2, m_{20}, m_{12}\}$
$T_3 = \{m_{01}, m_{12}, m_{20}\}$.

Subsequently, and as represented by Box 68 in FIG. 1, the centroid of each dome triangle is determined. Each of these centroids is designated a "dome triangle centroid", and an exemplary centroid is designated by the numeral 69 in FIG. 8. The dome triangle centroids are defined as follows:

$c_{T_0}$=centroid($T_0$)
$c_{T_1}$=centroid($T_1$)
$c_{T_2}$=centroid($T_2$)
$c_{T_3}$=centroid($T_3$).

Next, an axis line is defined for each of the dome triangles. This step is indicated by Box 70 in FIG. 1. Each axis line passes through the centroid of the corresponding dome triangle and the origin of the coordinate system 18. The axis lines are defined as follows:

$R_{T_0}$=ray(O, $c_{T_0}$)
$R_{T_1}$=ray(O, $c_{T_1}$)
$R_{T_2}$=ray(O, $c_{T_2}$)
$R_{T_3}$=ray(O, $c_{T_3}$).

As shown by the line designated 72 in FIG. 1, the method then returns to Box 34. However, in this iteration and in subsequent iterations, only the axis lines defined in Box 70 are used to calculate the moments in Box 34 and for finding the moment-minimizing axis as represented by Box 36. Therefore, the moments for this iteration forward are defined as follows:

$I_0$=moment(P,$R_{T_0}$)
$I_1$=moment(P,$R_{T_1}$)
$I_2$=moment(P,$R_{T_2}$)
$I_3$=moment(P,$R_{T_3}$).

Subsequently, and as represented by Box 36 in FIG. 1, the moment-minimizing axis is determined as follows:

$I_j = \min(|I_{F_0}|, |I_{F_1}|, |I_{F_2}|, |I_{F_3}|)$.

Note that absolute values are to be taken from the moments $I_{F_0}$, $I_{F_1}$, $I_{F_2}$, $I_{F_3}$ prior to finding the minimum, in case the moments are calculated in such a way as to result in negative values. The subscript j shall assume the value of the subscript assigned to the triangle associated with the moment-minimizing axis for the remainder of this iteration. Furthermore, the labels $v_0$, $v_1$, and $v_2$ shall be assigned arbitrarily to the vertices of the triangle associated with the moment-minimizing axis, and these vertices will be referred to as such for the remainder of this iteration.

Each iteration of the loop in FIG. 1, between Box 34 and Box 70, reduces the angle of accuracy determined in Box 44 and increases the precision afforded to the resultant determined long axis. Preferably, the fewest number of iterations is carried out to get the accuracy needed. However, the needed number of iterations may vary according to whether or not a polyhedron other than an icosahedron is used. The needed number of iterations may also vary according to initial conditions, such as the orientation of the object with respect to the orientation of the icosahedron.

As an additional alternative, the steps represented by Boxes 38, 44 and 46 may be omitted and replaced with a step that counts the number of iterations. For any given polyhedron, a predefined number of iterations can provide a desired accuracy so long as the tooth is sufficiently elongated to enable convergence on a moment-minimizing axis.

Figure 11:
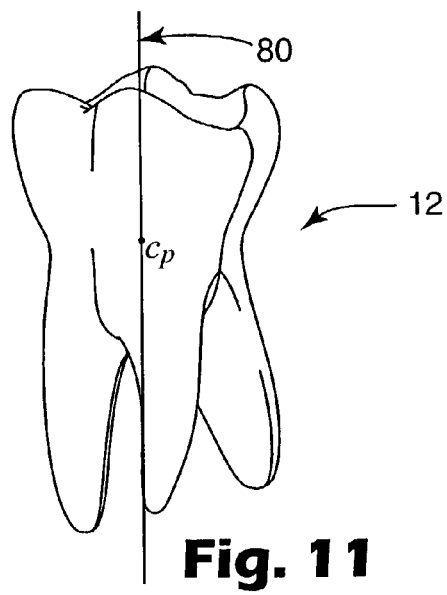
FIG. 11 is an illustration of the tooth depicted in FIGS. 2 and 3 along with a long axis that has been derived according to the method in FIG. 1.

FIG. 11 shows the tooth 12 along with a long axis 80 that has been determined by the method above. The method can also serve to determine the long axis of only a portion of the tooth provided that the portion is sufficiently elongated to enable the method to unambiguously determine the long axis.

The long axis of the tooth 12 as determined by the method set out in FIG. 1 can then be used for a variety of applications. For example, the long axis can be used to determine the facial axis point, or FA point, of the clinical crown. To find the FA point, a crown/root interface plane perpendicular to the long axis and approximating the gingival margin is determined along with a cusp tip or most occlusal point of the clinical crown. The mid-transverse plane of the clinical crown is then determined, which is perpendicular to the long axis and midway between the crown/root interface plane and the cusp tip. Next, the mid-frontal plane of the crown is determined, which includes the long axis of the tooth and separates the facial and lingual halves of the clinical crown. By definition, the mid-frontal plane is perpendicular to the mid-transverse plane. Additionally, the mid-sagittal plane of the crown is determined, which includes the long axis of the tooth and lies perpendicular to the mid-frontal plane, thus dividing the mesial and distal halves of the clinical crown. The FA point is then determined by finding the intersection of the mid-transverse plane, the mid-sagittal plane and the facial surface of the clinical crown.

The FA point can be used for accurate placement of an orthodontic appliance, such as a bracket, on the surface of the tooth (i.e., either the patient's actual tooth or a model of the patient's tooth). Optionally, the appliance need not be centered precisely on the FA point. However, the FA point serves as a valuable reference mark to position the appliance, whether or not the FA point coincides with the center of the appliance or is offset from the center of the appliance as may be desired by the practitioner.

The long axis of a tooth as determined by the method set out in FIG. 1 can also be used in a computer program for identifying the spatial relationship of a tooth to adjacent teeth or to all of the teeth along one or both of the dental arches. Additionally, the long axis may be used in a program for predicting the path of movement of a tooth during the course of orthodontic treatment. Moreover, the long axis may be used to determine the orientation of a tooth during intermediate steps of orthodontic treatment and/or at the conclusion of orthodontic treatment.

The long axis of the tooth as determined by the present invention can also be used in a computer program for constructing an indirect bonding tray. Indirect bonding trays are often desirable for placing appliances on the teeth at certain pre-selected locations without the necessity of substantial manual intervention. The indirect bonding tray can be constructed by, for example, a stereolithographic apparatus that makes the tray with recesses complemental to the shape of the patient's teeth while also orienting appliances connected to the tray at certain positions relative to the recesses. Examples of suitable indirect bonding trays and methods for making and using the same are described in U.S. Pat. No. 6,123,544 which is incorporated by reference herein.

Furthermore, the long axis of the tooth can be used, if desired, to make a custom appliance or modify standard appliances to facilitate treatment. For instance, brackets with certain patient-specific characteristics such as a certain torque and/or angulation can be made. The long axis determination, along with other digital information relating to the teeth, may also be used to form an archwire for use with appliances. Automated, robotic equipment may be used in carrying out such processes.

Those skilled in the art may recognize that a number of variations and additions to the methods set out above may be provided without departing from the gist of the invention. Accordingly, the invention should not be deemed limited by the detailed description set out above, but instead only by a fair scope of the claims that follow along with their equivalents.

The invention claimed is:

1. A method of determining the long axis of an object comprising:
   defining a polyhedron that surrounds a point representing the centroid of an object;
   defining, for at least some of the faces of the polyhedron, an axis line that passes through the face and also through the point representing the centroid of the object;
   calculating the moment of the object about each axis line;
   selecting the axis line that corresponds to the smallest calculated moment;
   controlling the object within a three-dimensional (3D) modeling environment based upon the determined long axis; and
   constructing an article in accordance with the selected axis lines.

2. A method of determining the long axis of an object according to claim 1 wherein the act of defining a polyhedron includes the act of defining a polyhedron having a center that coincides wit the point representing the centroid of the object.

3. A method of determining the long axis of an object according to claim 2 wherein the act of defining a polyhedron tat surrounds a point representing the centroid of the object includes the act of establishing a polyhedron that surrounds the point and the act of translating the data representing the object relative to the polyhedron so that the center of the polyhedron coincides with the point.

4. A method of determining the long axis of an object according to claim 1 wherein the act of defining, for at least some of the faces of the polyhedron, an axis line that passes through the face includes the act of defining an axis line that passes through the centroid of the face.

5. A method of determining the long axis of an object according to claim 1 wherein the act of defining a polyhedron comprises the act of defining an icosahedron.

6. A method of determining the long axis of an object according to claim 1 and including the acts of:
   defining a reference line that passes through a vertex of the face corresponding to the selected axis line;
   determining the angle between the reference line and the selected axis line; and
   comparing the determined angle to a pre-selected value.

7. A method of determining the long axis of an object according to claim 6 and including the acts of:
   subdividing into projected sections the face corresponding to the selected axis line if the determined angle is greater than the pre-selected value;
   defining, for at least some of the subdivided sections of the face, a subdivided section axis line that passes through the subdivided section and also passes through the point representing the centroid of the object;
   calculating the moment of the object about each subdivided section axis line; and
   selecting the subdivided section axis line that corresponds to the smallest calculated moment.

8. A method of determining the long axis of an object according to claim 7 wherein the act of defining, for at least some of the subdivided sections of the face, a subdivided section axis line includes the act of defining a subdivided section axis line that passes through the centroid of the subdivided section.

9. A method of determining the long axis of an object according to claim 7 wherein the act of subdividing into sections the face corresponding to the selected axis line comprises the act of subdividing the face into triangular sections.

10. A method of determining the long axis of an object according to claim 7 wherein the projected sections have vertices that are tangent to a reference sphere that is also tangent to the vertices of the polyhedron.

11. A method of determining the long axis of an object according to claim 10 wherein the polyhedron is an icosahedron and wherein the projected sections are triangles.

12. A method of determining the long axis of an object according to claim 7 and including the acts of:
   defining a reference line that passes through a vertex of the subdivided section corresponding to the selected axis line;
   determining the angle between the reference line and the selected subdivided section axis line; and
   comparing the determined angle between the reference line and the selected subdivided section axis line to a pre-selected value.

13. A method of determining the long axis of an object according to claim 12 and including the act of further subdividing the subdivided section if the determined angle between the reference line and the selected subdivision section axis line is greater than the pre-selected value.

14. A method of determining the long axis of an object according to claim 1 wherein the object is a tooth.

15. A method of determining the long axis of an object according to claim 14 and including the additional act of providing a set of data representing the shape of a patient's actual tooth.

16. A method of determining the long axis of an object according to claim 14 and including the additional act of providing a set of data representing the shape of a model of a patient's tooth.

17. A method of determining the long axis of an object according to claim 14 and including the additional ant of providing a set of data representing points on external surfaces of the tooth.

18. A method of determining the long axis of an object according to claim 14 and including the additional act of providing a set of data representing points distributed throughout the volume of the tooth.

19. A method of determining the long axis of an object according to claim 14 and including the additional act of using the selected axis line to determine the facial axis point of the clinical crown.

20. A method of determining the long axis of an object according to claim 14 and including the additional act of using the selected axis line to place an orthodontic appliance on the tooth or on a model of the tooth.

21. A method of determining the long axis of an object according to claim 14 and including the additional act of using die selected axis line to determine a desired orientation of the tooth at a stage of orthodontic treatment.

22. A method of determining the long axis of an object according to claim 14 and including the additional act of using the selected axis line to diagnose a malocclusion.

23. A method of determining the long axis of an object according to claim 14 and including the additional act of using the selected axis line to predict movement of the tooth during the course of orthodontic treatment.

24. A method of detennining the long axis of an object according to claim 1 wherein the moment is the moment of inertia.

25. A method of determining the long axis of an object according to claim 7 wherein the moment is the moment of inertia.

26. The method of claim 1, wherein controlling the object comprises displaying the object within the 3D modeling environment using the determined Long axis as a reference.

27. The method of claim 1, further comprising using the selected axis line for orthodontic treatment of a patient.

28. The method of claim 1, wherein the orthodontic appliance comprises an indirect bonding tray.

29. The method of claim 1, wherein the article comprises an orthodontic appliance.

30. The method of claim 1, further comprising using the determined long axis for placement of an orthodontic appliance.

31. The method of claim 1, further comprising predicting a path of movement of a tooth during the course of an orthodontic treatment based on the determined long axis.

32. The method of claim 1, further comprising identifying a spatial relationship of a tooth to another tooth represented within the 3D modeling environment based on the determined long axis.

33. A method comprising:
defining a polyhedron that surrounds a point representing the centroid of a tooth;
defining, for at least some of the faces of the polyhedron, an axis line that passes trough the face and also trough the point representing the centroid of the tooth;
calculating the moment of the tooth about each axis line;
selecting the axis line that corresponds to the smallest calculated moment; and
predicting a path of movement of the tooth during the course of an orthodontic treatment based on the determined long axis; and
using the selected axis line and the predicted path of movement to place an orthodontic appliance on the tooth or a model of the tooth.

34. A method of determining the long axis of an object comprising:
defining a polyhedron that surrounds a point representing the centroid of an object;
defining, for at least some of the faces of the polyhedron, an axis line that passes through the face and also through the point representing the centroid of the object;
calculating the moment of the object about each axis line;
selecting the axis line that corresponds to the smallest calculated moment; and
constructing an article in accordance with the selected axis line.

35. A computer-implemented system comprising:
a computing device having software executing thereon that processes digital data to determine a long axis of an object by:
defining a polyhedron that surrounds a point representing the centroid of an object;
defining, for at least some of the faces of the polyhedron, an axis line that passes through the face and also through the point representing the centroid of the object;
calculating the moment of the object about each axis line;
selecting the axis line that corresponds to the smallest calculated moment; and
using the selected axis line to place an orthodontic appliance on the tooth or a model of the tooth.

36. A method comprising:
defining a polyhedron that surrounds a point representing the centroid of an object;
defining, for at least some of the faces of the polyhedron, an axis line that passes through the face and also through the point representing the centroid of the object;
calculating the moment of the object about each axis line;
selecting the axis line that corresponds to the smallest calculated moment as the long axis of the object;
controlling the object within a three-dimensional (3D) modeling environment based upon the selected axis line; and
using the selected axis line to fabricate an indirect bonding tray.

37. A computer-readable medium comprising a computer program that performs a method of:
defining a polyhedron that surrounds a point representing the centroid of an object;
defining, for at least some of the faces of the polyhedron, an axis line that passes through the face and also through the point representing the centroid of the object;
calculating the moment of the object about each axis line;
selecting the axis line that corresponds to the smallest calculated moment;
placing an orthodontic appliance on a tooth or a model of a tooth in accordance with the selected axis line.

38. A method of determining the long axis of an object comprising:
(a) providing a set of data representing the shape of an object in a multi-dimensional environment;
(b) defining a polyhedron that surrounds a point representing the centroid of the object;
(c) defining, for at least some of the faces of the polyhedron, an axis line that passes through the face and also through the point representing the centroid of the object;
(d) calculating the moment of the object about each axis line;
(e) selecting the axis line that corresponds to the smallest calculated moment;

(f) determining the angle between the selected axis line and a reference line defined by the point representing the centroid of the object and a vertex of the polyhedron face associated with the selected axis line;

(g) comparing the determined angle to a pre-selected value;

(h) recursively following, by subdividing into sections the face corresponding to the selected axis line, at least some of acts a–g if the determined angle is greater than the pre-selected value;

(i) processing the data representing the object within the multi-dimensional environment in accordance with the determined long axis; and (j) constructing an article in accordance with the determined long axis.

39. A method of determining the long axis of an abject according to claim 38 and including the act of recursively following, by further subdivision of the subdivided face sections, at least some of acts a–g if the determined angle corresponding to the first subdivision of the face is greater than the pre-selected value.

40. A method of determining the long axis of an object according to claim 38 wherein the act of defining, for at least some of the faces of the polyhedron, an axis line that passes through the face includes the act of defining an axis line that passes trough the centroid of the face.

41. A method of determining the long axis of an object according to claim 38 wherein the act of defining a polyhedron comprises the act of defining an icosahedron.

42. A method of determining the long axis of an object according to claim 38 wherein the moment is the moment of inertia.

43. A computer-readable medium comprising computer program that performs a method of:

(a) accessing a set of data representing the shape of an object;

(b) defining a polyhedron that surrounds a point representing the centroid of the object;

(c) defining, for at least some of the faces of the polyhedron, an axis line that passes through the face and also through the point representing the centroid of the object;

(d) calculating the moment of the object about each axis line;

(e) selecting the axis line that corresponds to the smallest calculated moment;

(f) determining the angle between the selected axis line and a reference line defined by the point representing the centroid of the object and a vertex of the polyhedron face associated with the selected axis line;

(g) comparing the determined angle to a pre-selected value;

(h) recursively following, by subdividing into sections the face corresponding to the selected axis line, at least some of acts a–g if the determined angle is greater than the pre-selected value; and (i) placing an orthodontic appliance on a tooth or a model of a tooth in accordance with the selected axis line.

44. A method of determining the long axis of a tooth comprising:

(a) accessing a set of data representing the shape of a tooth within a modeling environment;

(b) defining a polyhedron that surrounds a point representing the centroid of the tooth;

(c) defining, for at least some of the faces of the polyhedron, an axis line that passes through the face and also through the point representing the tooth centroid;

(d) calculating the moment of the tooth about each axis line;

(e) selecting the axis line that corresponds to the smallest calculated moment;

(f) determining the angle between the selected axis line and a reference line defined by the point representing the centroid of the tooth and a vertex of the polyhedron face associated with the selected axis line;

(g) comparing the determined angle to a pre-selected value;

(h) recursively following, by subdividing into sections the face corresponding to the selected axis line, at least some of acts a–g if the determined angle is greater than the pre-selected value; and (i) processing the data representing the tooth in accordance with the determined long axis to place an orthodontic appliance on the tooth or a model of the tooth.

45. A method of determining the long axis of a tooth according to claim 44 and including the act of recursively following, by further subdivision of the subdivided face sections, at least some of acts a–g if the determined angle corresponding to the first subdivision of the face is greater than the pre-selected value.

46. A method of determining the long axis of a tooth according to claim 44 wherein the act of defining, for at least some of the faces of the polyhedron, an axis line that passes through the face includes the act of defining an axis line that passes through the centroid of the face.

47. A method of determining the long axis of a tooth according to claim 44 wherein the act of defining a polyhedron comprises the act of defining an icosahedron.

48. A method of determining the long axis of a tooth according to claim 44 and including the additional act of providing a set of data representing the shape of a patient's actual tooth.

49. A method of determining the long axis of a tooth according to claim 44 and including the additional act of providing a set of data representing the shape of a model of a patient's tooth.

50. A method of determining the long axis of a tooth according to claim 44 and including the additional act of providing a set of data representing points on external surfaces of the tooth.

51. A method of determining the long axis of a tooth according to claim 44 and including the additional act of providing a set of data representing points distributed throughout the volume of the tooth.

52. A method of determining the long axis of a tooth according to claim 44 and including the additional act of using the selected axis line to determine the facial axis point of the clinical crown.

53. A method of determining the long axis of a tooth according to claim 44 and including the additional act of using the selected axis line to determine a desired orientation of the tooth at a stage of orthodontic treatment.

54. A method of detennining the long axis of a tooth according to claim 44 and including the additional act of using the selected axis line to diagnose a malocclusion.

55. A method of determining the long axis of a tooth according to claim 44 and including the additional act of using the selected axis line to predict movement of the tooth during the course of orthodontic treatment.

56. A method of determining the long axis of a tooth according to claim 44 and including the additional act of using the selected axis line to fabricate an indirect bonding tray.

57. A method of determining the long axis of a tooth according to claim 44 wherein the moment is the moment of inertia.

58. A computer-readable medium comprising a computer program that performs a method of:
- (a) providing a set of data representing the shape of a tooth;
- (b) defining a polyhedron that surrounds a point representing the centroid of the tooth;
- (c) defining, for at least some of the faces of the polyhedron, an axis line that passes through the face and also through the point representing the tooth centroid;
- (d) calculating the moment of the tooth about each axis line;
- (e) selecting the axis line that corresponds to the smallest calculated moment;
- (f) detennining the angle between the selected axis line and a reference line defined by the point representing the centroid of the tooth and a vertex of the polyhedron face associated with the selected axis line;
- (g) comparing the determined angle to a pre-selected value;
- (h) recursively following, by subdividing into sections the face corresponding to the selected axis line, at least some of acts a–g if the determined angle is greater than the pre-selected value; and
- (i) constructing an orthodontic appliance in accordance with the selected axis line.

* * * * *

UNITED STATES PATENT AND TRADEMARK OFFICE
CERTIFICATE OF CORRECTION

PATENT NO. : 7,033,327 B2 Page 1 of 2
APPLICATION NO. : 10/243362
DATED : April 25, 2006
INVENTOR(S) : Raby, Richard E.

It is certified that error appears in the above-identified patent and that said Letters Patent is hereby corrected as shown below:

Page 2, Other Publications
Line 25, Delete "88," and insert -- 86, --, therefor.
Line 26, Delete "GalleryI," and insert -- Gallery!, --, therefor.

Column 3
Line 37, Delete "sonic" and insert -- some --, therefor.

Column 7
Line 30, Delete "$R_{F1}$=ray(0, $_{CF1}$)" and insert -- $R_{F1}$=ray(O, $_{CF1}$) --, therefor.

Column 11
Line 49, In Claim 2, after "coincides" delete "wit" and insert -- with --, therefor.
Line 53, In Claim 3, delete "tat" and insert -- that --, therefor.

Column 12
Line 63, In Claim 17, after "additional" delete "ant" and insert -- act --, therefor.

Column 13
Line 13, In Claim 21, after "using" delete "die" and insert -- the --, therefor.
Line 23, In Claim 24, delete "detennining" and insert -- determining --, therefor.
Line 31, In Claim 26, delete "Long" and insert -- long --, therefor.
Line 53, In Claim 33, after "passes" delete "trough" and insert -- through --, therefor.
Line 53, In Claim 33, after "also" delete "trough" and insert -- through --, therefor.

Column 14
Line 51, In Claim 37, after "moment;" and insert -- and --.

UNITED STATES PATENT AND TRADEMARK OFFICE
CERTIFICATE OF CORRECTION

PATENT NO. : 7,033,327 B2
APPLICATION NO. : 10/243362
DATED : April 25, 2006
INVENTOR(S) : Raby, Richard E.

It is certified that error appears in the above-identified patent and that said Letters Patent is hereby corrected as shown below:

Column 15
Line 26, In Claim 40, after "passes" delete "trough" and insert -- through --, therefor.

Column 16
Line 57, In Claim 54, delete "detennining" and insert -- determining --, therefor.

Column 18
Line 1, In Claim 58, delete "detennining" and insert -- determining --, therefor.

Signed and Sealed this

First Day of August, 2006

JON W. DUDAS
*Director of the United States Patent and Trademark Office*